US009018001B2

(12) United States Patent
Hesketh et al.

(10) Patent No.: US 9,018,001 B2
(45) Date of Patent: Apr. 28, 2015

(54) KIT FOR THE OPTIMISATION OF PROTEIN SYNTHESIS/SECRETION

(75) Inventors: John E. Hesketh, Jesmond (GB); Ian Fraser Pryme, Bergen (NO); Beate Stern, Bergen (NO); Hanne Ravneberg, Bergen (NO)

(73) Assignee: UniTargeting Research AS, Bergen (NO)

( * ) Notice: Subject to any disclaimer, the term of this patent is extended or adjusted under 35 U.S.C. 154(b) by 281 days.

(21) Appl. No.: 13/122,378

(22) PCT Filed: Oct. 1, 2009

(86) PCT No.: PCT/IB2009/007021
§ 371 (c)(1),
(2), (4) Date: Apr. 1, 2011

(87) PCT Pub. No.: WO2010/038145
PCT Pub. Date: Apr. 8, 2010

(65) Prior Publication Data
US 2011/0262905 A1 Oct. 27, 2011

Related U.S. Application Data

(60) Provisional application No. 61/102,131, filed on Oct. 2, 2008.

(30) Foreign Application Priority Data

Oct. 2, 2008 (SE) ........................ 0802078
Mar. 9, 2009 (SE) ........................ 0900297

(51) Int. Cl.
| | | |
|---|---|---|
| C12Q 1/68 | (2006.01) | |
| C12N 15/62 | (2006.01) | |
| C07K 14/435 | (2006.01) | |
| C07K 16/00 | (2006.01) | |
| C12P 21/02 | (2006.01) | |

(52) U.S. Cl.
CPC ........ *C12N 15/625* (2013.01); *C07K 14/43509* (2013.01); *C07K 16/00* (2013.01); *C07K 2319/02* (2013.01); *C12N 2830/48* (2013.01); *C12P 21/02* (2013.01)

(58) Field of Classification Search
USPC ..................................................... 435/320.1
See application file for complete search history.

(56) References Cited

FOREIGN PATENT DOCUMENTS

WO WO 02/068660 9/2002
WO WO 2005/001099 1/2005

OTHER PUBLICATIONS pTRE2hyg Vector Information; pp. 1-2; published May 7, 2007.*
pTRE2hyg sequence; http://www.clontech.com/xxclt_ibcGetAttachment.jsp?cItemId=41928&minisite=10020&secItmd=15366; pp. 1-5; published May 10, 2011.*
*Gaussia princeps* luciferase sequence; http://www.ncbi.nlm.nih.gov/nuccore/ay015993; Accession Nos. AY15993, GI: 12621053; publicly available Oct. 18, 2005.*
Stratagene Catalog; pp. 39; published 1998.*
Stern et al.; Improving mammalian cell factories: The selection of signal peptide has a major impact on recombinant protein synthesis and secretion in mammalian cells; Trends in Cell & Molecular Biology; vol. 1; pp. 1-17; 2006.*
International Search Report for International Application No. PCT/IB2009/007021 mailed Mar. 26, 2010.
Chu et al. "Industrial choices for protein production by large-scale cell culture." *Curr. Opin. Bio.* vol. 12. 2001. pp. 180-187.
Emmanouilides et al. "Anti-VEGF antibody bevacizumab (Avastin) with 5FU/LV as third line treatment for colorectal cancer." *Tech Coloproctol.* vol. 8. 2004. pp. S50-S52.
Knappskog et al. "The level of synthesis and secretion of *Gaussia princeps* luciferase in transfected CHO cells is heavily dependent on the choice of signal peptide." *J. of Biotec.* vol. 128. 2007. pp. 705-715.
Kwaks et al. "Employing epigenetics to augment the expression of therapeutic proteins in mammalian cells." *TRENDS in Biotech.* vol. 24. No. 3. 2006. pp. 137-142.
Ozanne. "Getting the most out of producing therapeutic biologics." *Pharm. Tech. Europe.* 2006. pp. 59-61.
Patridge et al. "Competition between the signal sequence and 3'UTR localization signal during redirection of beta-globin mRNA to the endoplasmic reticulum: implications for biotechnology." *Cytotechnology.* vol. 30. 1999. pp. 37-47.
Serarslan et al. "Widespread maculopapular rash due to intramuscular interferon beta-1a during the treatment of multiple sclerosis." *Multiple Sclerosis.* vol. 14. 2008. pp. 259-261.
Stern et al. "Improving mammalian cell factories: The selection of signal peptide has a major impact on recombinant protein synthesis and secretion in mammalian cells." *TRENDS.* vol. 2. 2007. pp. 1-17.
Stern et al. "UTRtech™: Exploiting mRNA Targeting to increase protein secretion from mammalian cells." *Cell Tech. for Cell Prod.* 2007. pp. 261-268.
Tröβe et al. "Vectors encoding seven oikosin signal peptides transfected into CHO Cells Differ Greatly in Mediating *Gaussia* luciferase and Human Endostatin Production although mRNA levels are largely unaffected." *Gene Regulation and Systems Biology* vol. 1 2007. pp. 303-312.
Veyrune et al. "A localization signal in the 3' untranslated region of c-*myc* mRNA targets c-*myc* mRNA and β-globin reporter sequences to the perinuclear cytoplasm and cytoskeletal-bound polysomes." *J. of Cell Sci.* vol. 109. 1996. pp. 1185-1194.
Wurm. "Production of recombinant protein:therapeutics in cultivated mammalian cells." *Nature Biotec.* vol. 22. No. 11. 2004. pp. 1393-1398.

\* cited by examiner

*Primary Examiner* — James Ketter
*Assistant Examiner* — Antonio Galisteo Gonzalez
(74) *Attorney, Agent, or Firm* — Merchant & Gould P.C.

(57) ABSTRACT

The invention relates to a kit to be used for the identification of a secretion cassette, which in eukaryotic cells gives rise to a higher level of synthesis/secretion of a protein of interest, the coding sequence of which being flanked by the first and the second set of genetic elements, respectively, compared to the other secretion cassettes present in the kit containing the coding sequence at the corresponding position, as well as to a method wherein the kit is used and the use of the kit, whereby the best secretion cassette will be obtained.

11 Claims, 2 Drawing Sheets

SEQUENCE LISTING

```
<160> NUMBER OF SEQ ID NOS: 26

<210> SEQ ID NO 1
<211> LENGTH: 31
<212> TYPE: DNA
<213> ORGANISM: Artificial Sequence
<220> FEATURE:
<223> OTHER INFORMATION: 3' end of human cytomegalovirus major
      immediate-early promoter enhancer

<400> SEQUENCE: 1
tatataagca gagctcgttt agtgaaccgt c                                    31

<210> SEQ ID NO 2
<211> LENGTH: 159
<212> TYPE: DNA
<213> ORGANISM: Artificial Sequence
<220> FEATURE:
<223> OTHER INFORMATION: 5' UTR derived partly from Gaussia princeps
      luciferase
```

<400> SEQUENCE: 2

```
agatcgcctg gagacgccat ccacgctgtt ttgacctcca tagaagacac cgggaccgat      60
ccagcctccg cggccccgaa ttcgagctcg gtacccgggg atcccccggg ctgcaggaat     120
tcggcacgag ggtactcaaa gtatcttctg gcagggaaa                             159
```

<210> SEQ ID NO 3
<211> LENGTH: 51
<212> TYPE: DNA
<213> ORGANISM: Artificial Sequence
<220> FEATURE:
<223> OTHER INFORMATION: Signal sequence derived from Metridia longa
      luciferase with mutations

<400> SEQUENCE: 3

```
atggatataa aggttgtctt tgcccttgtt ttctgcgcat tggttcaggc a               51
```

<210> SEQ ID NO 4
<211> LENGTH: 48
<212> TYPE: DNA
<213> ORGANISM: Artificial Sequence
<220> FEATURE:
<223> OTHER INFORMATION: Signal sequence derived from Oikopleura dioica
      oikosin 1 with mutations

<400> SEQUENCE: 4

```
atgctgctgt tggttgcgct tctccttggg cttgcccatg ggtactcc                   48
```

<210> SEQ ID NO 5
<211> LENGTH: 48
<212> TYPE: DNA
<213> ORGANISM: Artificial Sequence
<220> FEATURE:
<223> OTHER INFORMATION: Signal sequence derived from Oikopleura dioica
      oikosin 1 with mutations

<400> SEQUENCE: 5

```
atgctgctgt tggttgcgct tctccttggg cttgccgctg ggtactcc                   48
```

<210> SEQ ID NO 6
<211> LENGTH: 48
<212> TYPE: DNA
<213> ORGANISM: Artificial Sequence
<220> FEATURE:
<223> OTHER INFORMATION: Signal sequence derived from Oikopleura dioica
      oikosin 1 with mutations

<400> SEQUENCE: 6

```
atgctgctgc tgtccgccct gctgctggga ctggctgccg gctacagc                   48
```

<210> SEQ ID NO 7
<211> LENGTH: 54
<212> TYPE: DNA
<213> ORGANISM: Artificial Sequence
<220> FEATURE:
<223> OTHER INFORMATION: Signal sequence derived from homo sapiens
      chymotrypsinogen B2 with mutations

<400> SEQUENCE: 7

```
atggctttcc tctggctcct ctcctgctgg gccctcctgg gtaccacctt cggc            54
```

<210> SEQ ID NO 8
<211> LENGTH: 54
<212> TYPE: DNA
<213> ORGANISM: Artificial Sequence -continued

```
<220> FEATURE:
<223> OTHER INFORMATION: Signal sequence derived from homo sapiens
      chymotrypsinogen B2 with mutation

<400> SEQUENCE: 8
atggctttcc tctggctcct cttctgctgg gccctcctgg gtaccacctt cggc        54

<210> SEQ ID NO 9
<211> LENGTH: 153
<212> TYPE: DNA
<213> ORGANISM: Artificial Sequence
<220> FEATURE:
<223> OTHER INFORMATION: 3'UTR derived from Gaussia princeps luciferase

<400> SEQUENCE: 9
tcctaataga atactgcata actggatgat gatatactag cttattgctc ataaaatggc    60
cattttttgt aacaaatcga gtctatgtaa ttcaaaatac ctaattaatt gttaatacat   120
atgtaattcc tataaatata atttatgcaa tcc                                153

<210> SEQ ID NO 10
<211> LENGTH: 186
<212> TYPE: DNA
<213> ORGANISM: Artificial Sequence
<220> FEATURE:
<223> OTHER INFORMATION: 3'UTR derived from homo sapiens serum albumin

<400> SEQUENCE: 10
catctacatt taaaagcatc tcagcctacc atgagaataa gagaaagaaa atgaagatca    60
aaagcttatt catctgtttt cttttcgtt ggtgtaaagc caacaccctg tctaaaaaac    120
ataaatttct ttaatcattt tgcctctttt ctctgtgctt caattaataa aaatggaaa    180 gaatct                                                              186

<210> SEQ ID NO 11
<211> LENGTH: 357
<212> TYPE: DNA
<213> ORGANISM: Artificial Sequence
<220> FEATURE:
<223> OTHER INFORMATION: Poly(A)-site downstream region derived from
      Oryctolagus cuniculus beta-globin

<400> SEQUENCE: 11
aatagtgtgt gggaattttt tgtgtctctc actcggaagg acatatggga gggcaaatca    60
tttaaaacat cagaatgagt atttggttta gagtttggca acatatgccc atatgctggc   120
tgccatgaac aaaggttggc tataaagagg tcatcagtat atgaaacagc ccctgctgt    180 ccattcctta ttccatagaa aagccttgac ttgaggttag atttttttta tattttgttt   240
tgtgttattt ttttctttaa catccctaaa attttcctta catgttttac tagccagatt   300
tttcctcctc tcctgactac tcccagtcat agctgtccct cttctcttat ggagatc      357

<210> SEQ ID NO 12
<211> LENGTH: 56
<212> TYPE: DNA
<213> ORGANISM: Artificial Sequence
<220> FEATURE:
<223> OTHER INFORMATION: 5'UTR derived from Gaussia princeps luciferase

<400> SEQUENCE: 12
attcagacaa ctgaatccaa aaggaaaggt actcaaagta tcttctggcc gccacc        56

<210> SEQ ID NO 13
```

```
<211> LENGTH: 51
<212> TYPE: DNA
<213> ORGANISM: Artificial Sequence
<220> FEATURE:
<223> OTHER INFORMATION: Signal sequence derived from Gaussia princeps
      luciferase with mutations

<400> SEQUENCE: 13
atgggagtca aagttctgtt tgccctgatc tgcatcgctg tggccgaggc c          51

<210> SEQ ID NO 14
<211> LENGTH: 48
<212> TYPE: DNA
<213> ORGANISM: Artificial Sequence
<220> FEATURE:
<223> OTHER INFORMATION: Signal sequence derived from Oikopleura dioica
      oikosin 1 with mutations

<400> SEQUENCE: 14
atgctgctgt tgtcagcgct tctccttggg cttgcctttg ggtactcc              48

<210> SEQ ID NO 15
<211> LENGTH: 136
<212> TYPE: DNA
<213> ORGANISM: Artificial Sequence
<220> FEATURE:
<223> OTHER INFORMATION: 3'UTR derived from homo sapiens serum albumin

<400> SEQUENCE: 15
atgaagatca aagcttatt catctgtttt cttttcgtt ggtgtaaagc caacaccctg   60
tctaaaaaac ataaatttct ttaatcattt tgcctctttt ctctgtgctt caattaataa  120
aaaatggaaa gaatct                                                 136

<210> SEQ ID NO 16
<211> LENGTH: 185
<212> TYPE: DNA
<213> ORGANISM: Artificial Sequence
<220> FEATURE:
<223> OTHER INFORMATION: 3'UTR derived from homo sapiens serum albumin

<400> SEQUENCE: 16
catcacattt aaaagcatct cagcctacca tgagaatccg agaaagaaaa tgaagagaaa  60
aagcttattc atctgttttc ttttcgttg gtgtaaagcc aacaccctgt ctaaaaaaca  120
taaatttctt taatcatttt gcctctttt ctctgtgctt caattaataaa aaatggaaag  180 aatct                                                             185

<210> SEQ ID NO 17
<211> LENGTH: 17
<212> TYPE: PRT
<213> ORGANISM: Artificial Sequence
<220> FEATURE:
<223> OTHER INFORMATION: Signal protein sequence

<400> SEQUENCE: 17

Met Asp Ile Lys Val Val Phe Ala Leu Val Phe Cys Ala Leu Val Gln
1               5                   10                  15

Ala

<210> SEQ ID NO 18
<211> LENGTH: 16
<212> TYPE: PRT
<213> ORGANISM: Artificial Sequence
<220> FEATURE:
```

-continued

<223> OTHER INFORMATION: Signal protein sequence

<400> SEQUENCE: 18

Met Leu Leu Leu Val Ala Leu Leu Leu Gly Leu Ala His Gly Tyr Ser
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Signal protein sequence

<400> SEQUENCE: 19

Met Leu Leu Leu Val Ala Leu Leu Leu Gly Leu Ala Ala Gly Tyr Ser
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Signal protein sequence

<400> SEQUENCE: 20

Met Leu Leu Leu Ser Ala Leu Leu Leu Gly Leu Ala Ala Gly Tyr Ser
1               5                   10                  15

<210> SEQ ID NO 21
<211> LENGTH: 18
<212> TYPE: PRT
<213> ORGANISM: Artificial Sequence
<220> FEATURE:
<223> OTHER INFORMATION: Signal protein sequence

<400> SEQUENCE: 21

Met Ala Phe Leu Trp Leu Leu Ser Cys Trp Ala Leu Leu Gly Thr Thr
1               5                   10                  15

Phe Gly

<210> SEQ ID NO 22
<211> LENGTH: 18
<212> TYPE: PRT
<213> ORGANISM: Artificial Sequence
<220> FEATURE:
<223> OTHER INFORMATION: Signal protein sequence

<400> SEQUENCE: 22

Met Ala Phe Leu Trp Leu Leu Phe Cys Trp Ala Leu Leu Gly Thr Thr
1               5                   10                  15

Phe Gly

<210> SEQ ID NO 23
<211> LENGTH: 16
<212> TYPE: PRT
<213> ORGANISM: Artificial Sequence
<220> FEATURE:
<223> OTHER INFORMATION: Signal protein sequence

<400> SEQUENCE: 23

Met Leu Leu Leu Val Ala Leu Leu Leu Gly Leu Ala Ala Gly Tyr Ser
1               5                   10                  15

<210> SEQ ID NO 24
<211> LENGTH: 18

```
<212> TYPE: PRT
<213> ORGANISM: Artificial Sequence
<220> FEATURE:
<223> OTHER INFORMATION: Signal protein sequence

<400> SEQUENCE: 24

Met Ala Phe Leu Trp Leu Leu Ser Cys Trp Ala Leu Leu Gly Thr Thr
1               5                   10                  15

Phe Gly

<210> SEQ ID NO 25
<211> LENGTH: 17
<212> TYPE: PRT
<213> ORGANISM: Artificial Sequence
<220> FEATURE:
<223> OTHER INFORMATION: Signal protein sequence

<400> SEQUENCE: 25

Met Gly Val Lys Val Leu Phe Ala Leu Ile Cys Ile Ala Val Ala Glu
1               5                   10                  15

Ala

<210> SEQ ID NO 26
<211> LENGTH: 16
<212> TYPE: PRT
<213> ORGANISM: Artificial Sequence
<220> FEATURE:
<223> OTHER INFORMATION: Signal protein sequence

<400> SEQUENCE: 26

Met Leu Leu Leu Ser Ala Leu Leu Leu Gly Leu Ala Phe Gly Tyr Ser
1               5                   10                  15
```

KIT FOR THE OPTIMISATION OF PROTEIN SYNTHESIS/SECRETION

FIELD OF INVENTION

The invention relates to a kit to be used for the identification of a secretion cassette, which in eukaryotic cells gives rise to a higher level of synthesis/secretion of a protein of interest, the coding sequence of which being flanked by the first and the second set of genetic elements, respectively, compared to the other secretion cassettes present in the kit containing the coding sequence at the corresponding position, as well as to a method wherein the kit is used and the use of said kit, whereby the best secretion cassette will be identified.

BACKGROUND OF INVENTION

There is at present a huge demand for recombinant proteins in research and therapy, and it is anticipated that this demand will further expand during the next 20 years (Chu and Robinson, 2001). Amongst the most dominant proteins produced are growth factors, monoclonal antibodies, hormones and blood coagulation factors that are mainly used for clinical and pharmaceutical purposes. Specific examples of protein-based treatments are the therapy of cancer with monoclonal antibodies like bevacizumab (Avastin™) directed against vascular endothelial growth factor (VEGF) to inhibit angiogenesis, or the therapy of multiple sclerosis with interferon beta-1a (Avonex™) (Emmanouilides et al, 2004; Serarslan et al, 2008).

Currently the increasing demand for therapeutic proteins poses a significant challenge. The availability of proteins produced from natural resources is strongly limited and thus high-yield production of recombinant proteins is imperative. This is a complicated task, starting with the choice of an appropriate host organism. Comparatively simple proteins like insulin or bovine growth hormone (BGH) can be made in prokaryotic cell systems (Kwaks et al, 2006). For more complex molecules like monoclonal antibodies (mAbs) and other glycosylated proteins, eukaryotic cells are indispensable. Their properties of being able to perform correct post-translational modifications and carry out accurate protein folding and assembly are important to prevent any immunogenic effect in humans.

The production of recombinant proteins using eukaryotic cells is extremely expensive and inefficient in comparison to the production with prokaryotic cells. Nevertheless, more than 60% of all therapeutic proteins are produced in mammalian cells like Chinese Hamster Ovary (CHO) cells, Mouse Myeloma (NS0) cells, Human Embryonic Kidney (HEK-293) cells or Human Retina derived cells (PER.C6) (Ozanne, 2008; Wurm, 2004). This explains the considerable interest in developing new technologies to improve mammalian cell culture production processes. The optimisation can occur at various levels, e.g. improvement in the culture medium composition and process control as well as through vector and host cell line engineering. Regarding the improvement of the production cell lines, a post-transcriptional approach focusing on specific targeting elements in messenger RNA (mRNA) and their effect on the enhancement of protein synthesis and secretion (Knappskog et al, 2007; Stern et al, 2007a,b; Tröβe et al, 2007) is an important new area not yet fully exploited.

The mRNA targeting elements comprise the signal sequence (SS) preceding the coding sequence (cds) of a protein of interest and the 5' and 3' untranslated regions (UTRs). Partridge et al (1999) observed a competition between a selected SS and 3'UTR in mediating mRNA targeting to distinct polysomes. This illustrated the importance of choosing a "correct" pair of SS and 3'UTR when designing a secretion cassette. The SS encodes the signal peptide (SP), a short, cleavable polypeptide located at the N-terminus of secreted and membrane proteins, which directs protein synthesis to the membrane of the rough endoplasmic reticulum (RER), a prerequisite to attain secretion of a protein. Knappskog et al (2007) investigated the effect of different SPs derived from mammalian secretory proteins on the synthesis/secretion level of a reporter protein. Unexpectedly, the SPs derived from human albumin and interleukin-2 proved to be far inferior to that derived from the luciferase of the marine copepod *Gaussia princeps*. The results clearly demonstrated that the choice of SS to be used in a secretion cassette is imperative when aiming at improving protein production. Further experiments showed that SPs derived from a wide variety of sources (marine, mammalian, prokaryotic) varied greatly in their ability to promote high level protein production (Stern et al, 2007a,b; Tröβe et al, 2007). Furthermore, it has become quite clear that substantial amounts of mRNA coding for a recombinant protein can be present in transfected cells without this necessarily leading to a high level of secreted products (Knappskog et al, 2007; Tröβe et al, 2007). Thus the common strategy of merely increasing mRNA levels of a protein of interest may not be a fruitful approach.

SUMMARY OF THE INVENTION

The invention is focused on high-level synthesis/secretion of proteins in eukaryotic cell lines, wherein there is a need of increasing synthesis/secretion to be able to produce the protein of interest to a high amount. Thereby it will be possible to produce the protein of interest at a commercial scale. Many different genetic elements regulate the expression of a gene such as the mRNA targeting elements located upstream and downstream of the cds of the gene to be expressed. A gene may be upregulated as well as downregulated whereby extensive upregulation may result in that the cell in which the expression occur silences said gene. This implies that there is a window in which optimisation of expression can occur, making it difficult to fine-tune a eukaryotic cell with respect to high-level protein production.

When a gene is to be expressed in a eukaryotic cell system, the nature and combination of mRNA targeting elements flanking its cds have been shown to greatly influence the level of synthesis/secretion of the encoded protein. Further, it became evident that there is no single combination of specific mRNA targeting elements favourable for all proteins. Thus a subset of different combinations needs to be evaluated for each protein. Since there are many different genetic elements available and a plethora of variants thereof that could be combined in different ways, it is impossible for a person skilled in the art to find out by trial and error which genetic elements that need to be optimised. One would have expected that if a gene is to be expressed in a mammalian system then at least for example the SS/SP should be of mammalian origin for it to be efficiently expressed.

Based on the above, the inventors have developed a kit-based approach, where a kit comprises a certain number of secretion cassettes containing different pre-defined mRNA targeting element combinations to be used for screening for the best cassette in the kit, mediating the highest synthesis/secretion level of the particular protein of interest.

In a first aspect the invention relates to a kit comprising at least two different secretion cassettes, wherein each of said secretion cassettes comprises a first set of genetic elements comprising at least a promoter 3' end, a 5'UTR and a SS and a second set of genetic elements comprising at least a 3'UTR and a poly(A)-site downstream region, wherein said first set is upstream (at the 5' end) of said second set and wherein at least one of the elements is different between the various cassettes.

In a second aspect the invention relates to a method for the optimisation of protein synthesis/secretion comprising the steps of: providing the kit mentioned above, inserting a cds of a protein of interest into said secretion cassettes between said first and said second set of genetic elements, inserting said secretion cassette into a vector, introducing the secretion cassettes/vectors into a eukaryotic host cell line, analysing the levels of said synthesis/secretion achieved with the different cassettes in the cells of said host cell line, which can be either transiently or stably transfected, comparing said synthesis/secretion levels of said protein obtained with the different secretion cassettes and determining which secretion cassette present in said kit mediates the highest synthesis/secretion level of said protein of interest.

By using the invented kit and method it is possible to identify a secretion cassette which mediates synthesis/secretion of a protein of interest to a higher level compared to the level achieved with the other secretion cassette(s) present in the kit. Since the secretion cassettes present in a kit will normally have been chosen based on the criterion of being successful with respect to mediating increased production of a model protein(s), there is a strong likelihood that the best cassette identified for the protein of interest will considerably increase its production.

DETAILED DESCRIPTION OF THE INVENTION

Definitions

In the context of the present application and invention the following definitions apply:

The term "nucleotide sequence" is intended to mean a continuous sequence of two or more nucleotides. The nucleotide may be DNA, RNA as well as a mixture thereof, and of natural, semi-synthetic or synthetic origin.

The term "coding sequence (cds)" is intended to mean a nucleotide sequence which begins with, and includes, a start codon or first codon of the mature protein and ends with, and includes, a stop codon.

The term "mRNA targeting element" is intended to mean a nucleotide sequence constituting the upstream and downstream untranslated regions of a gene (5'UTR and 3'UTR) and the signal sequence (SS) preceding the cds of a gene encoding either a secretory or membrane protein.

The term "genetic element" is intended to mean an mRNA targeting element as well as any other nucleotide sequence involved in transcriptional and/or translational regulation of a gene, including promoter and poly(A)-site downstream region.

The term "5' untranslated region (5'UTR)" is intended to mean the nucleotide sequences on the upstream side of any cds not translated into protein. It extends from the transcription initiation site to just before the start codon of a cds. The 5' UTR may contain sequences that regulate translation efficiency, mRNA stability and/or mRNA targeting.

The term "3' untranslated region (3'UTR)" is intended to mean the nucleotide sequences on the downstream side of any cds not translated into protein. It extends from the first nucleotide after the stop codon of a cds to just before the poly(A) tail of the mRNA. The 3' UTR may contain sequences that regulate translation efficiency, mRNA stability, mRNA targeting and/or polyadenylation.

The terms "signal peptide (SP)" and "signal sequence (SS)" are intended to mean an N-terminal polypeptide targeting a protein for translocation across the endoplasmic reticulum membrane in eukaryotic cells and cleaved off during the translocation process, and the nucleotide sequence which codes for this polypeptide, respectively. Signal sequences may also be called targeting signals, signal sequences, transit peptides, or localization signals in the literature.

The term "promoter 3' end" is intended to mean the nucleotide sequence which begins with, and includes, the TATA box of the promoter and ends at, but not includes, the transcription initiation site.

The term "poly(A)-site downstream region" is intended to mean the nucleotide sequence located downstream of the nucleotide sequence transcribed into mRNA, providing signal(s) required for proper mRNA processing.

The term "secretion cassette" is intended to mean a nucleotide sequence containing at least a specific promoter 3' end, a specific 5'UTR, a specific SS, a specific 3'UTR and a specific poly(A)-site downstream region, such as the first and the second set of nucleotide sequences shown below.

The term "secretion vector" is intended to mean any vector containing a secretion cassette. The terms "vector" and "plasmid" are used interchangeably in the literature.

The term "protein of interest" is intended to mean any polypeptide encoded by a gene or any protein encoded by one or more gene(s), and of which there are a need for obtaining an increased quantity for specific purposes and which are to be produced in a recombinant manner by cultivated eukaryotic cells.

The Kit

The invention relates to a kit to be used for the optimisation of protein synthesis/secretion. By specific combinations of different mRNA targeting elements together with the optimisation of the elements by DNA sequence improvement through e.g. codon adjustment to the host system, and/or by the introduction of specifically selected nucleotide/amino acid mutations, the cassettes within the kit will mediate an increased synthesis/secretion level of the encoded protein to be produced in a eukaryotic system. The kit comprising at least two different secretion cassettes, wherein each of said secretion cassettes comprises a first set of genetic elements comprising at least a promoter 3' end, a 5'UTR and a SS, wherein said SS comprises codon optimisation and/or a mutation(s), and a second set of genetic elements comprising at least a 3'UTR and a poly(A)-site downstream region, wherein said first set is upstream of said second set and wherein at least one of the elements is different between the various cassettes. By the use of such a kit comprising a number of secretion cassettes comprising different genetic elements in specific combinations, such as the example shown in Table 1, it will always be possible to find at least one secretion cassette which synthesises/secretes a protein of interest to a higher level compared to the other secretion cassette(s) present in the kit. Further, since the secretion cassettes present in a kit will normally have been chosen based on the criterion of being successful with respect to mediating increased production of a model protein(s), the best cassette identified for the protein of interest will considerably increase its production. In the kit there may be two or more secretion cassettes, such as 2, 3, 4, 5, 6 etc. different secretion cassettes. A specific example being a kit comprising 6 different secretion cassettes, such as that shown below in example 1 and 2.

The secretion cassettes present in such a kit comprise a number of genetic elements, wherein the promoter 3' end may have the nucleotide sequence given in SEQ ID NO:1; the 5'UTR may have the nucleotide sequence given in SEQ ID NO:2 or SEQ ID NO:12; the SS may have the nucleotide sequences given in SEQ ID NO:3, 4, 5, 6, 7, 8, 13 or 14; the 3'UTR may have the nucleotide sequences given in SEQ ID NO:9, 10, 15 or 16; the poly(A)-site downstream region may have the nucleotide sequence given in SEQ ID NO:11.

The secretion cassette may also include an entire promoter, such as the human cytomegalovirus major immediate-early promoter/enhancer (hCMV promoter), instead of just a promoter 3' end.

Further, the secretion cassettes may comprise at least one or more cloning site(s) comprising one or more restriction enzyme recognition site(s) enabling e.g. the possibility to clone the cds of a protein of interest, i.e. a protein for which there is a need of increasing the synthesis/secretion level, into the cassette, or to clone the secretion cassette into a vector. Examples being, a cloning site in between said first and said second set of genetic elements as well as a cloning site at each end of the secretion cassette.

The secretion cassettes may also be present in a suitable vector, such that all the different secretion cassettes are placed within an identical backbone vector. One example being shown below wherein the sole differences between the secretion vectors containing the six cassettes will be those regarding the SS elements and the 5'/3'UTR elements.

Accordingly the invention relates to a method for the optimisation of protein synthesis/secretion comprising the steps of: providing the kit comprising the secretion cassettes as defined above, inserting the cds of a protein of interest into said secretion cassettes, inserting said secretion cassette into a vector, introducing the secretion cassettes/vectors into a eukaryotic host cell line, assessing the levels of said synthesis/secretion of said protein in said cells, which can be either transiently or stably transfected, comparing said synthesis/secretion levels of said protein obtained with the different secretion cassettes and determining which secretion cassette present in said kit mediates the highest synthesis/secretion level of said protein of interest.

The insertion of the cds of a protein of interest into a secretion cassette and the insertion of the cassette into a vector may be done in a manner well-known for a person skilled in the art, such as by the use of a suitable method disclosed in the well-known manuals Sambrook J et al. (Molecular Cloning: A Laboratory Manual (Third Edition), Cold Spring Harbor Laboratory Press, Cold Spring Harbor, N.Y., 2000) and Ausubel F M et al. (Current Protocols in Molecular Biology, Wiley InterScience, 2008). The secretion vector may then be introduced into a eukaryotic host cell line and the cells containing the secretion vector may be selected by cultivating the cells in a medium containing a selection agent(s), such as hygromycin B phosphotransferase, or puromycin N-acetyl transferase, depending on the particular selection marker present in the vector used, and stably transfected pools or clonal cell lines generated in a manner well-known for a person skilled in the art, such as by the use of a suitable method disclosed in the above mentioned manuals by Sambrook J et al. and Ausubel F M et al.

Examples of different eukaryotic cells and/or cell lines that may be transfected with the secretion vectors include animal cells, plant cells, fungal or yeast cells. One example being that the animal cell is a mammalian cell. Other examples are that said mammalian cell is selected from the group consisting of primate-, monkey- and rodent-derived cells. Other examples are that said primate cell is of *Homo sapiens* or *Pan troglodytes* origin, said monkey cell is of *Cercopithecus aethiops* origin, and said rodent cell is of *Cricetulus griseus, Mesocricetus auratus, Rattus norvegicus, Oryctolagus cuniculus* or *Mus musculus* origin. Other examples are that said mammalian cell belongs to any of the cell line families CHO, NS0, HEK-293, myeloma, NOS, COS, BHK, HeLa and PER.C6.

The cells are grown for a suitable time period to generate transiently transfected cells, stably transfected cell pools or clonal cell lines. The cells will then be evaluated regarding the level with which they synthesise/secrete the protein of interest. This may be done by the use of an enzyme-linked immunosorbent assay (ELISA), a bioluminescence assay, Western blot analysis, Protein A HPLC, or by any other suitable method as disclosed e.g. in the above mentioned manuals by Sambrook J et al. and Ausubel F M et al. The cell line that shows the highest synthesis/secretion level of the protein of interest will be identified and the respective secretion cassette can then be further used e.g. for large-scale production of the protein of interest.

The following examples are intended to illustrate, but not to limit, the invention in any manner, shape, or form, either explicitly or implicitly.

EXAMPLES

Example 1

Insertion of the Cds of a Model Protein into Secretion Cassettes #1-6

Figure 1:
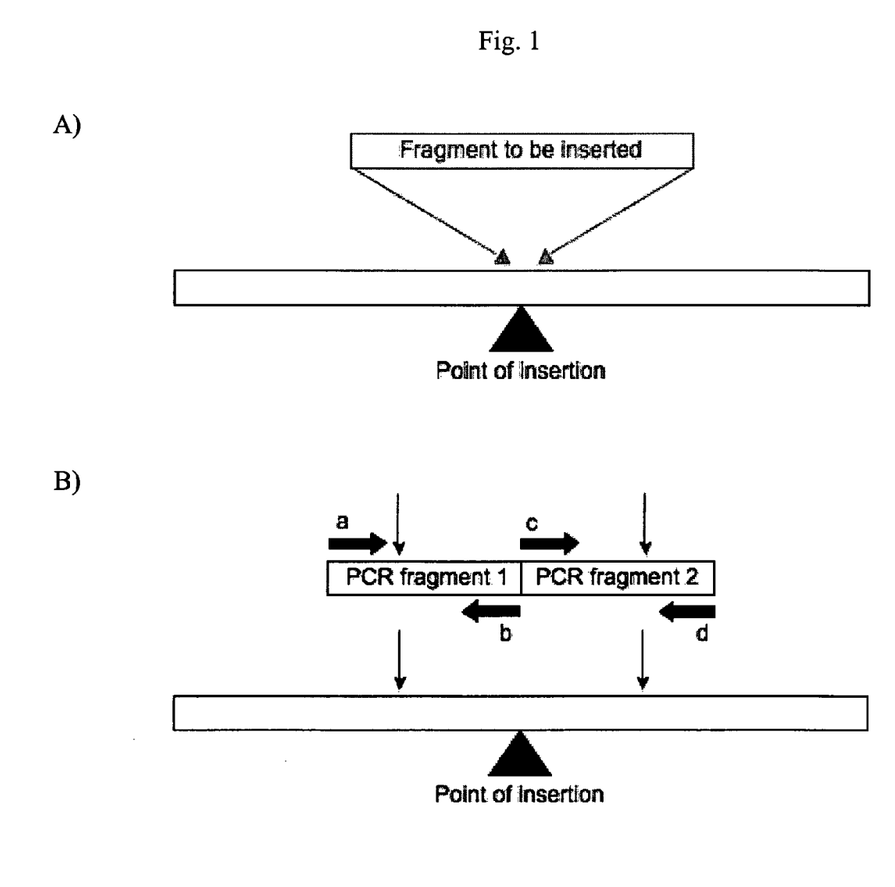
FIG. 1 shows the principle of a PCR based procedure for the "seamless" insertion of a DNA fragment (consisting of e.g. the cds of the protein of interest) into another DNA fragment (consisting e.g. of the secretion cassette) or the "seamless" insertion of a DNA fragment (consisting e.g. of the secretion cassette harbouring the cds of the protein of interest) into a vector (panel A). The procedure does not incorporate any linker sequences and does not require restriction enzyme recognition sites to be present at specific positions. In successive steps two PCR fragments are generated consisting of the nucleotide sequence regions at either side of the point of insertion, each containing a unique restriction enzyme recognition site (panel B) and one PCR product is generated composed of the fragment to be inserted and two flanking sequences, introduced with the primer "tails", matching the sequences flanking the point of insertion (panel C). In two additional PCR reactions, fragments 1-3 are assembled generating fragments 4 and 5 (panel D). Fragment 5 contains two unique restriction enzyme recognition sites at it's ends, which can be used to clone or subclone the fragment into the recipient vector. Horizontal arrows indicate primers, specified by letters; waved lines indicate primer "tails"; long vertical arrows indicate restriction enzyme recognition sites.

The model proteins chosen are the naturally secreted luciferase from *Gaussia princeps* and a human IgG mAb. The nucleotide sequences of the cds's of the luciferase and the heavy chain (HC) and light chain (LC) of the mAb are derived from cDNA. The cds's without their native SSs were inserted between the SSs and the 3'UTRs of the secretion cassettes #1-6, respectively (see Table 1). All SSs in the cassettes carry a mutation with respect to the original sequences from which they are derived. In some cases the SS mutation(s) is/are non-silent, thus resulting in a mutation(s) also in the corresponding SP (see Table 2). Insertion of each cds was performed in a "seamless" manner, such that the first nucleotide of the cds preceding the native SS was fused directly to the last nucleotide of the respective SSs in the cassettes and the last nucleotide of the cds to the first nucleotide of the respective 3'UTRs in the cassettes. The method used is outlined in FIG. 1.

Vector Construction

The secretion cassettes generated including the cds of *Gaussia* luciferase, HC and LC, respectively, were inserted into the pTRE2hyg expression vector (Clontech Laboratories) immediately 5' to the TATA box of the $P_{hCMV*-1}$ promoter, such that the last nucleotide before the TATA box in the vector was fused directly to the first nucleotide of the promoter 3' end in each cassette. The method used is outlined in FIG. 1.

Generation of Stably Transfected Cells

CHO AA8 Tet-Off cells (Clontech Laboratories) were grown and propagated according to the manufacturer's recommendations. $4 \times 10^5$ cells were transfected with the different secretion vectors using the MATra method (IBA BioTAGnology) according to the manufacturer's recommendations. The HC- and LC-encoding vectors containing the same cassettes, respectively, were cotransfected. Selection for stable cell pools was started 24 h post-transfection by applying 400 µg/ml hygromycin B phosphotransferase (luciferase- and LC-encoding vectors) and 10 µg/ml puromycin N-acetyl transferase (HC-encoding vector) to the cell culture medium for three weeks. In parallel with the secretion vectors, reference vectors, also based on pTRE2hyg and harbouring a reference cassette immediately 5' to the TATA box of the

TABLE 1

Composition of six secretion cassettes included in the kit and the nucleotide sequence IDs of their respective genetic elements.

| # | Promoter 3' end | 5'UTR | SS | Site for cds | 3'UTR | Poly(A)-site downstream region |
|---|---|---|---|---|---|---|
| 1 | SEQ ID NO: 1 | SEQ ID NO: 2 | SEQ ID NO: 3 | | SEQ ID NO: 9 | SEQ ID NO: 11 |
| 2 | SEQ ID NO: 1 | SEQ ID NO: 2 | SEQ ID NO: 4 | | SEQ ID NO: 9 | SEQ ID NO: 11 |
| 3 | SEQ ID NO: 1 | SEQ ID NO: 2 | SEQ ID NO: 5 | | SEQ ID NO: 9 | SEQ ID NO: 11 |
| 4 | SEQ ID NO: 1 | SEQ ID NO: 2 | SEQ ID NO: 6 | | SEQ ID NO: 9 | SEQ ID NO: 11 |
| 5 | SEQ ID NO: 1 | SEQ ID NO: 2 | SEQ ID NO: 7 | | SEQ ID NO: 9 | SEQ ID NO: 11 |
| 6 | SEQ ID NO: 1 | SEQ ID NO: 2 | SEQ ID NO: 8 | | SEQ ID NO: 10 | SEQ ID NO: 11 |

TABLE 2

Sequences of the SSs/SPs included in the kit (see Table 1).

| Sequence ID | SS sequence* | SP sequence* | SEQ ID |
|---|---|---|---|
| SEQ ID NO: 3 | ATG GAT ATA AAG GTT GTC TTT G<u>CC</u> CTT GTT TTC T<u>GC</u> GCA TTG GTT CAG GCA | MDIKVVF<u>A</u>LVF<u>C</u>ALVQA | 17 |
| SEQ ID NO: 4 | ATG CTG CTG TTG <u>GTT</u> GCG CTT CTC CTT GGG CTT GCC CAT GGG TAC TCC | MLLL<u>V</u>ALLLGLAHGYS | 18 |
| SEQ ID NO: 5 | ATG CTG CTG TTG <u>GTT</u> GCG GTT CTC CTT GGG CTT GCC <u>GCT</u> GGG TAC TCC | MLLL<u>V</u>ALLLGLA<u>A</u>GYS | 19 |
| SEQ ID NO: 6 | ATG CTG CTG <u>CTG</u> TCC GCC CT<u>G</u> CT<u>G</u> CT<u>G</u> GG<u>A</u> CT<u>G</u> GCT <u>GCC</u> GG<u>C</u> TAC <u>AGC</u> | MLLLSALLLGLA<u>A</u>GYS | 20 |
| SEQ ID NO: 7 | ATG GC<u>C</u> TT<u>T</u> CT<u>G</u> TGG CT<u>G</u> CT<u>G</u> TCC TG<u>T</u> TGG GC<u>T</u> CT<u>G</u> CTG GG<u>C</u> ACC ACC TTC GGC | MAFLWLLSCWALLGTTFG | 21 |
| SEQ ID NO: 8 | ATG GCT TTC CTC TGG CTC CTC T<u>TC</u> TGC TGG GCC CTC CTG GGT ACC ACC TTC GGC | MAFLWLL<u>F</u>CWALLGTTFG | 22 |

*mutated bases/amino acids with respect to wild-type bases/amino acids are underlined.

$P_{hCMV^{*}-1}$ promoter, were used for (co)transfection. The reference cassette contains the same promoter 3' end and poly (A)-site downstream region as the six secretion cassettes and the native *Gaussia* luciferase 5' UTR/SS and 3'UTR sequences flanking the cds's of luciferase, HC and LC, respectively.

Harvesting Samples $2\times10^5$ cells transfected with the different secretion vectors or reference vectors were seeded in 6-well plates, each well containing 2 ml of fresh medium, and medium samples collected after 24 h. To avoid interference from detached cells, all medium samples were centrifuged at 425 rcf for 10 min at 4° C., and the supernatant fluids were transferred to fresh tubes. Cells in the same wells were scraped off and counted. Medium samples were assayed for luciferase activity and mAb amount.

Luciferase Activity Assay

Luciferase activity was measured as Relative Light Units (RLUs) emitted when the samples, placed in the bottom of the wells of a white microtiter reading plate, were mixed with a coelentrazine solution (Prolume), in a Plate Chameleon V Microplate Reader (Hidex). Samples were measured in three parallel aliquots and the raw data obtained corrected for dilutions made and cell number. The luciferase activity of the reference construct was set to 100%.

ELISA for mAb Quantification

A sandwich ELISA was performed according to recognised laboratory procedure using the purified mAb as a standard. Anti-human IgG lambda light chain HRP-conjugated detection antibody and 3,3',5,5'-tetramethylbenzidine (TMB) developing solution were used for colorimetric HRP-based ELISA detection. The absorbance was read at 450 nm using a Plate Chameleon V Microplate Reader (Hidex). Samples were measured in three parallel aliquots and the raw data obtained corrected for dilutions made and cell number. The mAb amount of the reference construct was set to 100%.

Identification of the Best Secretion Cassettes for *Gaussia* Luciferase and mAb

Figure 2:
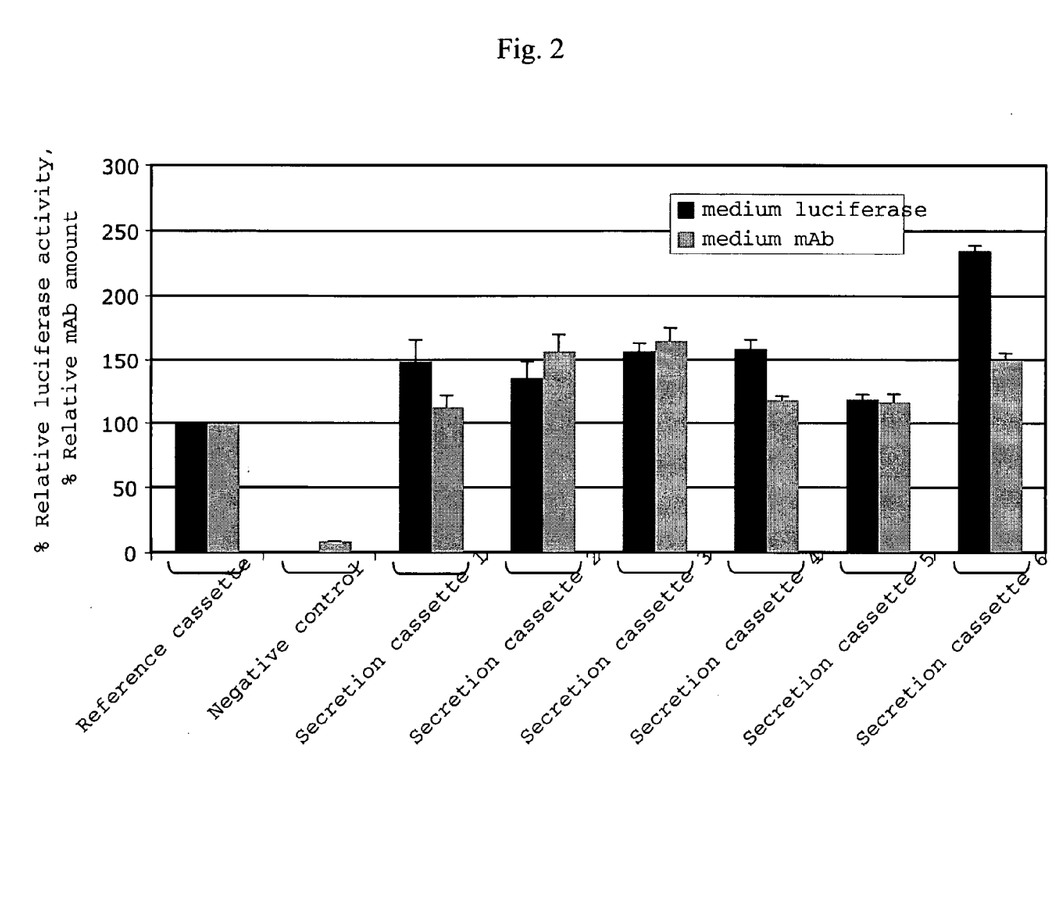
FIG. 2 shows the different secretion levels of two model proteins, *Gaussia princeps* luciferase and a mAb, the cds's of which are incorporated in 7 different cassettes (the reference cassette and six secretion cassettes), respectively, each present in the same backbone vector. Luciferase activity and mAb amount in medium samples of CHO cell pools stably transfected with the vectors harbouring the cassettes were measured and all measurements calculated in relation to the activity/amount in the medium samples of cells transfected with the vectors containing the reference cassette, which was set to 100%. The results shown are from one experiment with the standard deviations calculated from three parallel measurements. They represent the results obtained from three independently generated stable cell pools. The reference cassette was initially the "best performer"; it is based on mRNA targeting elements of the *Gaussia princeps* luciferase gene (Knappskog et al, 2007). The six secretion cassettes are those presented in Example 1 (#1-6, see Table 1).

In FIG. 2 the results are shown from one experiment, representative of three independent transfection experiments with the six secretion cassettes and the reference cassette. All cells stably transfected with the different secretion vectors show a higher level of luciferase/mAb secretion than the cells stably transfected with the reference vectors. The highest level for luciferase was obtained with secretion cassette #6 and the highest level for mAb with secretion cassette #3. Since all six secretion cassettes are superior to the reference cassette for both model proteins, it can be anticipated that they present a powerful tool kit to achieve enhanced secretion also for other proteins.

Example 2

Insertion of the Cds of a Model Protein into Secretion Cassettes #7-12

The model proteins chosen are the naturally secreted luciferase from *Gaussia princeps* and a human IgG mAb. The nucleotide sequences of the cds's of the luciferase and the heavy chain (HC) and light chain (LC) of the mAb are derived from cDNA. The cds's without their native SSs were inserted between the SSs and the 3'UTRs of the secretion cassettes #7-12, respectively (see Table 3). All SSs in the cassettes carry a mutation(s) with respect to the original sequences from which they are derived. In some cases the SS mutation(s) is/are non-silent, thus resulting in a mutation(s) also in the corresponding SP (see Table 4). Insertion of each cds was performed in a "seamless" manner, such that the first nucleotide of the cds preceding the native SS was fused directly to the last nucleotide of the respective SSs in the cassettes and the last nucleotide of the cds to the first nucleotide of the respective 3'UTRs in the cassettes. The method used is outlined in FIG. 1.

TABLE 3

Composition of six secretion cassettes included in the kit and the nucleotide sequence IDs of their respective genetic elements.

| # | Promoter 3' end | 5'UTR | SS | Site for cds | 3'UTR | Poly(A)-site downstream region |
|---|---|---|---|---|---|---|
| 7 | SEQ ID NO: 1 | SEQ ID NO: 12 | SEQ ID NO: 13 | | SEQ ID NO: 9 | SEQ ID NO: 11 |
| 8 | SEQ ID NO: 1 | SEQ ID NO: 2 | SEQ ID NO: 13 | | SEQ ID NO: 10 | SEQ ID NO: 11 |
| 9 | SEQ ID NO: 1 | SEQ ID NO: 12 | SEQ ID NO: 13 | | SEQ ID NO: 15 | SEQ ID NO: 11 |
| 10 | SEQ ID NO: 1 | SEQ ID NO: 2 | SEQ ID NO: 14 | | SEQ ID NO: 9 | SEQ ID NO: 11 |
| 11 | SEQ ID NO: 1 | SEQ ID NO: 2 | SEQ ID NO: 5 | | SEQ ID NO: 10 | SEQ ID NO: 11 |
| 12 | SEQ ID NO: 1 | SEQ ID NO: 2 | SEQ ID NO: 7 | | SEQ ID NO: 16 | SEQ ID NO: 11 |

TABLE 4

Sequences of the SSs/SPs included in the kit (see Table 3).

| Sequence ID | SS sequence* | SP sequence* | SEQ ID |
|---|---|---|---|
| SEQ ID NO: 5 | ATG CTG CTG TTG G<u>TT</u> GCG CTT CTC CTT GGG CTT GCC <u>GCT</u> GGG TAC TCC | MLLL<u>V</u>ALLLGLA<u>A</u>GYS | 23 |
| SEQ ID NO: 7 | ATG GC<u>C</u> <u>TTT</u> C<u>T</u>G TGG C<u>T</u>G C<u>T</u>G TCC TG<u>T</u> TGG GC<u>T</u> C<u>T</u>G CTG GG<u>C</u> ACC ACC TTC GGC | MAFLWLLSCWALLGTTFG | 24 |

TABLE 4-continued

Sequences of the SSs/SPs included in the kit (see Table 3).

| Sequence ID | SS sequence* | SP sequence* | SEQ ID |
|---|---|---|---|
| SEQ ID NO: 13 | ATG GGA GT<u>C</u> AAA GTT CT<u>G</u> TTT GCC CT<u>G</u> AT<u>C</u> TG<u>C</u> AT<u>C</u> GCT GTG GCC GAG GCC | MGVKVLFALICIAVAEA | 25 |
| SEQ ID NO: 14 | ATG CTG CTG TTG TCA GCG CTT CTC CTT GGG CTT GCC <u>TTT</u> GGG TAC TCC | MLLLSALLLGLA<u>F</u>GYS | 26 |

*mutated bases/amino acids with respect to wild-type bases/amino acids are underlined.

The procedures used for "Vector construction", "Generation of stably transfected cells", "Harvesting samples", "Luciferase activity assay" and "ELISA" for mAb quantification are the same as those described in Example 1. The results obtained from three independent transfection experiments with the six secretion cassettes and the reference cassettes for luciferase and mAb are comparable with those presented in FIG. 2 (data not shown).

REFERENCES

Chu L and Robinson D K (2001). Industrial choices for protein production by large-scale cell culture. Curr. Opin. Biotechnol. 12:180-187.

Emmanouilides C, Pegram M, Robinson R, Hecht R, Kabbinavar F and Isacoff W (2004). Anti-VEGF antibody bevacizumab (Avastin) with 5FU/LV as third line treatment for colorectal cancer. Tech. Coloproctol. 8 Suppl 1: 50-52.

Knappskog S, Ravneberg H, Gjerdrum C, Tröβe C R, Stern B and Pryme I F (2007). The level of synthesis and secretion of Gaussia princeps luciferase in transfected CHO cells is heavily dependent on the choice of signal peptide. J. Biotechnol. 128: 705-715.

Kwaks T H and Otte A P (2006). Employing epigenetics to augment the expression of therapeutic proteins in mammalian cells. Trends Biotechnol. 24: 137-142.

Ozanne D (2008). Getting the most out of producing therapeutic biologics. Pharmaceutical Technology Europe 5 58-61.

Partridge K, Johannessen A, Tauler A, Pryme I F and Hesketh J E (1999). Competition between the signal sequence and a 3'UTR localisation signal during redirection of beta-globin mRNA to the endoplasmic reticulum: implications for biotechnology. Cytotechnology 30: 37-47.

Serarslan G, Okuyucu E, Melek I, Hakverdi S and Duman T (2008). Widespread maculopapular rash due to intramuscular interferon beta-1a during the treatment of multiple sclerosis. Mult. Scler. 14: 259-261.

Stern B, Olsen L C, Tröβe C R, Ravneberg H and Pryme I F (2007a). Improving mammalian cell factories The selection of signal peptide has a major impact on recombinant protein synthesis and secretion in mammalian cells. Trends in Cell and Molecular Biology 2: 1-17.

Stern B, Gjerdrum C, Knappskog S, Minsaas L, Nyland S. Olsen L C, Olsen L, Oveland E, Ravneberg H, Tröβe C R, Tveit A, Vollsund E, Hesketh J E, Tauler A and Pryme I F (2007b). UTRtech: Exploiting mRNA targeting to increase protein secretion from mammalian cells, In: Cell Technology for Cell Products, ed. R. Smith, pp. 261-268, Springer, Dordrecht. ISBN 9781402054754.

Tröβe C R, Ravneberg H, Stern B and Pryme I F (2007). Vectors encoding seven oikosin signal peptides transfected into CHO cells differ greatly in mediating Gaussia luciferase and human endostatin production although mRNA levels are largely unaffected. Gene Regulation and Systems Biology 1: 303-312.

Wurm F M (2004). Production of recombinant protein therapeutics in cultivated mammalian cells. Nat. Biotechnol. 22: 1393-1398.

The invention claimed is:

1. A kit for the optimization of the expression of a protein in a mammalian cell comprising at least 2 different secretion cassettes, wherein each secretion cassette comprises a first and a second set of genetic elements, wherein
   a. the first set of genetic elements comprises at least a promoter 3' end, a 5'UTR, and a signal sequence (SS), wherein each SS is selected from the group consisting of the nucleotide sequences of SEQ ID NO:3, 4, 5, 6, 8, 13 and 14; and
   b. the second set of genetic elements comprises at least a 3'UTR, wherein each 3'UTR is selected from the group consisting of the nucleotide sequences of SEQ ID NO:9, 10, 15 and 16, and a poly(A)-site downstream region;
   wherein the first set of genetic elements is upstream of the coding sequence of the protein and the second set of genetic elements is downstream of the coding sequence of the protein in a secretion vector.

2. The kit according to claim 1, wherein the kit comprises 3, 4, 5, 6, or more different secretion cassettes.

3. The kit according to claim 1, wherein each 5'UTR comprises the nucleotide sequence of SEQ ID NO:2 or 12.

4. The kit according to claim 1, wherein the poly(A)-site downstream region comprises the nucleotide sequence of SEQ ID NO:11.

5. The kit according to claim 1, wherein each secretion cassette is present in an identical vector backbone.

6. The kit according to claim 2, wherein each 5'UTR comprises the nucleotide sequence of SEQ ID NO:2 or 12.

7. The kit according to claim 2, wherein the poly(A)-site downstream region comprises the nucleotide sequence of SEQ ID NO:11.

8. The kit according to claim 2, wherein each secretion cassette is present in an identical vector backbone.

9. The kit according to claim 3, wherein the poly(A)-site downstream region comprises the nucleotide sequence of SEQ ID NO:11.

10. The kit according to claim 3, wherein each secretion cassette is present in an identical vector backbone.

11. The kit according to claim 4, wherein each secretion cassette is present in an identical vector backbone.

* * * * *